United States Patent [19]

Gindler

[11] 4,369,250

[45] Jan. 18, 1983

[54] FATTY ACID DETERMINATION

[75] Inventor: E. Melvin Gindler, Union City, Calif.

[73] Assignee: Sherwood Medical Industries Inc., St. Louis, Mo.

[21] Appl. No.: 288,989

[22] Filed: Jul. 31, 1981

[51] Int. Cl.³ .................. C12Q 1/34; C12Q 1/44; G01N 31/00

[52] U.S. Cl. .................... 435/18; 435/11; 435/19; 435/810; 435/4; 436/13; 436/71

[58] Field of Search ............ 435/4, 11, 18, 19, 810; 23/230 B, 909, 230 R; 252/352, 357, 408

[56] References Cited

U.S. PATENT DOCUMENTS

| | | | |
|---|---|---|---|
| 3,759,793 | 9/1973 | Stork et al. | 435/19 |
| 3,884,637 | 5/1975 | Gindler | 252/408 |
| 3,953,359 | 4/1976 | Gindler | 252/408 |
| 3,969,076 | 7/1976 | Wang | 252/408 |
| 3,992,149 | 11/1976 | Wang | 252/408 |
| 4,195,126 | 3/1980 | Hall | 435/11 |
| 4,239,649 | 12/1980 | Gindler et al. | 435/11 |

OTHER PUBLICATIONS

Rose et al, *The Condensed Chemical Dictionary*, Reinhold Book Corp., New York, 623 (1966) 7th Edition.

*Primary Examiner*—Esther M. Kepplinger
*Attorney, Agent, or Firm*—Wegner, McCord, Wood & Dalton

[57] ABSTRACT

A complex of a long chain cationic surfactant and an organic anionic dye is useful in demonstrating the presence of and determining the concentration of fatty acids, compounds which hydrolyze to liberate fatty acids, or the activity of hydrolaze enzymes which produce fatty acids from a substrate.

42 Claims, No Drawings

FATTY ACID DETERMINATION

BACKGROUND OF THE INVENTION

1. Field of the Invention

This invention relates to a method, reagent, and reagent kit utilizing a surfactant-dye complex for the demonstration and determination of free fatty acids, compounds which hydrolyze to yield fatty acids, and hydrolase enzymes which act on substrates to produce fatty acids.

2. Description of the Prior Art

Prior methods for determining fatty acids in liquid samples include titration with alkali, determination of the copper salt of such acids after extraction with a suitable solvent, and chromatographic procedures. Such methods are time-consuming and, in general, are not adaptable to rapid, automated analysis techniques.

Further, various methods exist for demonstrating and determining compounds which are hydrolyzable to yield free fatty acids, including triglycerides, other cholesterol esters, and phospholipids. Prior methods for such determinations include enzymic hydrolysis methods, saponification methods, extraction methods, and chromatographic procedures.

Such techniques generally involve a number of processing steps which render the determinations time-consuming and costly, and/or require more than one reagent.

Hall U.S. Pat. No. 4,195,126 (Mar. 25, 1980), the disclosure of which is hereby incorporated by reference, discloses a method for determining free fatty acids and compounds which hydrolyze to yield free fatty acids.

The Hall patent describes an albumin-dye complex which is substantially free of endogenous free fatty acids and which has been pre-treated with a fatty acid. According to the method of the Hall patent, free fatty acids react with the albumin-dye complex to displace dye from the complex, yielding an albumin-fatty acid complex and free dye, the concentration of which is measurable by changes in absorbance or fluorescence. The change in absorbance is thus proportional to the concentration of fatty acid in the sample.

The Hall patent's complex may be used in determining a component in a sample which is capable of being hydrolyzed to yield fatty acid. The component is hydrolyzed by a hydrolase enzyme to yield a fatty acid, which is then reacted with the albumin-dye complex to liberate dye, the concentration of which can be directly measured by the change in absorbance or fluorescence.

The Hall patent also discloses that the complex can be used to determine the activity of a hydrolase enzyme in a liquid sample by adding to the sample a known amount of a compound which is capable of being hydrolyzed to yield a fatty acid, along with a reagent including the albumin-dye complex. The fatty acid thus liberated reacts with the complex to yield free dye, the concentration of which can be measured by observation of the absorbance change.

The albumin-dye complex of the Hall patent is limited in its practical utility, however, since one or more commercially useful hydrolase enzymes, such as *Rhizopus arrhizus* lipase, is conventionally provided in ammonium sulphate suspension. It has been found that ammonium sulfate interferes with the color development reaction of the Hall complex, thus necessitating desalting and lyophilizing of the lipase preparation obtained from the manufacturer. The lyophilized lipase is stable for only about 48 hours at 4° C.

Further, it has been found that serum albumin depresses absorbance readings of the Hall reagent so that the absorbance of reagent-containing serum, without lipase, is lower than that of the reagent itself.

SUMMARY OF THE INVENTION

It is an object of the invention to overcome one or more of the problems described above.

According to the invention, a complex of a long chain cationic surfactant and an organic anionic dye is the effective component of a reagent for demonstrating or determining fatty acids. The reagent is useful in combination with a hydrolase enzyme for the determination of materials which are hydrolyzable to yield a fatty acid, and is useful in combination with a known amount of a hydrolyzable material to demonstrate and determine hydrolase enzyme activity in a sample.

The inventive reagent is highly stable, and its color development reaction is not interfered with by solvents and other materials found in commercially available hydrolase enzyme preparations. Thus, the hydrolase enzyme can be incorporated into, or used in combination with, the reagent directly as received from the manufacturer.

Only a single reagent is required, and allows rapid demonstration or determination of an unknown in a sample.

Other objects and advantages of the invention will be apparent from the following detailed description taken in conjunction with the appended claims.

DETAILED DESCRIPTION OF THE INVENTION

The method of the present invention is based upon the reaction between a surfactant-dye complex and free fatty acids wherein the dye component of the complex is liberated by substitution by the free fatty acid.

The strong color of the free dye is decreased in intensity by complexing with the surfactant, and liberation of the dye by fatty acid substitution causes a distinct, measurable color change of a sample containing the complex.

With the use of a reagent incorporating as an effective ingredient a surfactant-dye complex of the type referred to above and described in detail below, the presence and concentration of free fatty acids, or compounds hydrolyzable to yield free fatty acids, in a liquid sample may be easily determined, since the change in color resulting from fatty acid substitution for the dye in the complex is directly proportional to the concentration of fatty acid, or fatty acid yielding component, in the sample.

Hall U.S. Pat. No. 4,195,126 describes several types of components of blood serum which may be determined using an albumin-dye complex reagent, as follows:

A. For triglycerides:

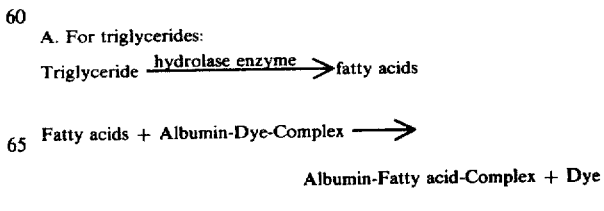

B. For Cholesterol esters:

-continued

Cholesterol ester $\xrightarrow{\text{hydrolase enzyme}}$ fatty acids

Fatty acids + Albumin-Dye Complex $\longrightarrow$
Albumin-Fatty acid-Complex + Dye C. For lecithin:

Lecithin $\xrightarrow{\text{hydrolase enzyme}}$ fatty acids

Fatty acids + Albumin-Dye-Complex $\longrightarrow$
Albumin-Fatty acid-Complex + Dye D. For ceramides:

Ceramide $\xrightarrow{\text{hydrolase enzyme}}$ fatty acids

Fatty acids + Albumin-Dye-Complex $\longrightarrow$
Albumin-Fatty acid-Complex + Dye E. For sphingomyelin:

Sphingomyelin $\xrightarrow{\text{enzymatic hydrolysis}}$ ceramide

Ceramide $\xrightarrow{\text{hydrolase enzyme}}$ fatty acids

Fatty acids + Albumin-Dye-Complex $\longrightarrow$
Albumin-Fatty acid-Complex + Dye F. For cerebrosides:

Cerebrosides $\xrightarrow{\text{enzymatic hydrolysis}}$ ceramide

Ceramide $\xrightarrow{\text{hydrolase enzyme}}$ fatty acids

Fatty acids + Albumin-Dye-Complex $\longrightarrow$
Albumin-Fatty acid-Complex + Dye G. For gangliosides:

Gangliosides $\xrightarrow{\text{enzymatic hydrolysis}}$ ceramide

Ceramide $\xrightarrow{\text{hydrolase enzyme}}$ fatty acids

Fatty acids + Albumin-Dye-Complex $\longrightarrow$
Albumin-Fatty acid-Complex + Dye The surfactant-dye complex of the invention may be readily employed for determining such components in an analogous manner.

The reagent and method of the invention is especially useful in the determination of fatty acid-containing components, especially such components of blood serum or other body fluids which are hydrolyzable to yield free fatty acids. Of special interest are those which are enzymatically hydrolyzable, as by simple contact with the hydrolase enzyme. Such materials include triglycerides, other cholesterol esters, etc.

The method of the invention is carried out by mixing with a liquid sample, either prior to or simultaneously with enzymatic hydrolysis thereof, a reagent comprising as its effective ingredient the surfactant-dye complex of the invention. The difference in absorbance observed prior to and subsequent to reaction is noted, and compared with calibration means to determine the concentration of fatty acid component in the sample.

The surfactant-dye complex-containing reagent of the invention can be used to determine the fatty acid content of essentially any aqueous medium containing fatty acids of chain length greater than about $C_{10}$ such as blood serum or plasma, cerebrospinal fluid, urine, and other body fluids.

If the fatty acids are present in the sample in the form of esters or amides, it is necessary to hydrolyze the materials as by contact with a suitable hydrolase enzyme specific to the compound in question.

The reactions between hydrolase enzymes and such compounds are well known, and are readily carried out by simple mixing of the enzyme and the compound in question.

Generally, the surfactant-dye complex of the invention comprises a complex of a long-chain cationic surfactant, and any of various organic anionic dyes.

The surfactant preferably comprises a quaternary ammonium cationic surfactant which includes a long hydrocarbon chain. A preferred example of such a surfactant is a di-ethoxylated long chain hydrocarbon methyl ammonium chloride surfactant marketed by Armak under the trademark Ethoquad® 18/25, and having the following structure:

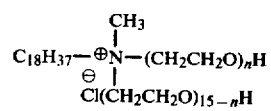

wherein n is an integer between about six and eight. Other suitable surfactants include the Rohm & Haas Co. surfactants Hyamine® 1622 or Hyamine® 10X, which have the following structures:

Hyamine® 1622:

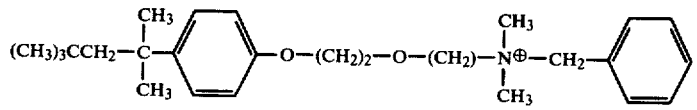

Hyamine® 10X:

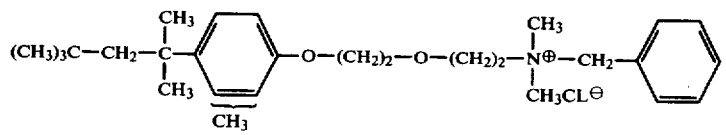

Any of various organic anionic dyes which are capable of complexing with cationic surfactants may be utilized. Suitable dyes include phthalein and sulfophthalein dyes, although other long chain anions such as carboxylates, sulfates, sulfonates, phosphates, and phosphonates are useful. Hall U.S. Pat. No. 4,195,126 identifies, at cols. 5-6, a wide variety of dyes useful in the albumin-dye complex of that patent. Such dyes are also useful in the reagent of this invention, and include compounds from the following classes: Azo, sulfonphthalein, triphenylmethane, fluorescein, naphthalenesulfonic acids, phenoxazine, anthraquinones, tricarbocyanine, indigo and acridine. Typical dyes include:

| Azo Dyes | Sulfonphthalein Dyes | Triphenylmethane Dyes |
|---|---|---|
| Amaranthum | Bromocresol Green | Coomassie Brilliant Blue ® |
| Orange I | Bromocresol Purple | Crystal Violet |
| Orange III | Bromophenol Blue | Malachite Green |
| Orange IV | Bromothymol Blue | |
| Congo Red | Chlorophenol Red | Fluorescein Dyes |
| Evans Blue | Cresol Red | Dichlorofluorescein |
| Naphthol Blue Black | Metacresol Purple | Fluorescein |
| HABA | Sulfobromophthalein | Fluoresceinisothiocyanate |
| Ponceau 3 R | Thymol Blue | |
| Ponceau S | | |
| Azocarmine B | | |

| Phenoxazine Dyes | Naphthalenesulfonic acid Dyes | Indigo Dyes |
|---|---|---|
| Resazurin | Anilinonaphthalene sulfonic acid | Indigo Carmine |
| Brilliant Cresyl Blue | Naphthol Yellow S | |

| Acridine Dyes | Anthraquinone Dyes | Tricarbocyanine Dyes |
|---|---|---|
| Acriflavine | Alizarin Red S | Indocyanine Green |

The preferred surfactant-dye complex is one including Ethoquad ® 18/25 and sulfobromphthalein in equimolar amounts, and may be prepared by simple mixing of dye and surfactant solutions.

A preferred hydrolase enzyme for hydrolyzing triglycerides and other materials to yield free fatty acids is *Rhizopus arrhizus* lipase, which has a relatively great specificity for triglycerides.

A preferred form of this enzyme is available from a French manufacturer, Sempa-Chime, 16 rue Broce, Paris in the form of an ammonium sulfate suspension.

One great advantage of the present invention is that the commercially available ammonium sulfate suspension may be used directly in a reagent in combination with the surfactant-dye complex. The albumin-dye complex of Hall U.S. Pat. No. 4,195,126 performs poorly in the presence of ammonium sulfate. Therefore, the lipase suspension must be desalted and lyophilized prior to use, and the lyophilized lipase is stable for only about 48 hours at 4° C. The ammonium sulfate lipase suspension, on the other hand, loses only about 6% of its activity in one year. Further, the cost of desalting and lyophilization is high and adds to the expense of the procedure.

In addition to being useful in the demonstration and determination of fatty acids and fatty acid yielding components, the reagent of the invention may be used to determine the concentration of a hydrolase enzyme in a sample. This determination is carried out by means of adding a reagent comprising a known amount of a triglyceride (or other fatty acid yielding hydrolyzable component) and the surfactant-dye complex to a sample containing an unknown amount of the enzyme, and comparing the degree of the resulting color change to calibration means.

In the determination of fatty acids and fatty acid yielding compounds, the fatty acid/complex reaction may be carried out either prior to or subsequent to hydrolysis, if the hydrolysis step is used. In such a case, a single reagent comprising the surfactant-dye complex and a lipase is added to a sample. Alternatively, the lipase may be added separately prior to or subsequent to addition of the color reagent.

The reaction is substantially instantaneous at room temperature, and is generally carried out at a pH of about 8.5 to 8.8.

In order to maintain pH in a desired range, a buffer may be utilized. An example of a preferred buffer composition is given below.

A sample size of only about 0.2 mL or less is required, and the reaction may be carried out at any desired temperature, preferably at room temperature or at 37° C. Only a single reagent is required.

The change in absorbance of the sample is proportional to the free fatty acid concentration thereof. Although the reaction is not necessarily stoichiometric, the change in absorbance can be readily compared to an aqueous or serum calibrator to which the reagent has been added, and is linear over the range of interest of the reaction.

Especially when a surfactant such as Ethoquad ® is being used, calibration is important since such surfactants tend to vary in composition from lot to lot. A useful calibrator comprises a composition marketed by ICI Americas under the mark Tween ® 80. Tween ® 80 is also known as Polysorbate 80 and may be characterized as a polyoxyethylene (20) sorbitan mono-oleate. Tween ® 80 hydrolyzes to yield oleic acid.

The preferred sulfobromphthalein dye is, in its free state, a deep purple. However, when complexed with Ethoquad ® or another long chain cationic surfactant, the intensity of the color decreases and is observed as a light blue. However, upon reaction with a free fatty acid so as to liberate dye, the free dye reverts to its deep purple color, and the resulting color change is distinct and readily measurable by standard spectrophotometric procedures, best at 580 nm.

One liter of a preferred complex reagent formulation, without lipase, is as follows:
25.13 gm Propionic acid
75.79 gm N-Methyl diethanolamine
0.307 mL Phenoxyethanol
61.4 mg Sulfobromphthalein Sodium Tetrahydrate (A)

143.1 mg Ethoquad ® 18/25
11.63 mg Chlorobutanol
0.284 mL 2-Propanol
2.00 gm Polyvinylpyrrolidone
0.100 gm EDTA (Free Acid, H4 EDTA)

This reagent may be combined directly with an ammonium sulfate suspension of lipase.

A preferred buffer solution for use in lipase hydrolysis is prepared as follows:

500 mL of a concentrate buffer solution in deionized water contains 34.04 gm imidazole, 29.6 gm propionic acid and 10.0 gm trishydroxymethylaminomethane hydrochloride. A working buffer solution (100 mL) in deionized water contains 20.0 mL of the concentrated buffer solution and 5.0 gm Pluronic® 10R8 (BASF Wyandotte).

A reagent kit for the use of the method and reagent of the invention comprises, in a single package, first and second containers. The first container contains an aqueous acidic solution of the surfactant-dye complex as given above, and the second container contains a buffer solution for use in lipase hydrolysis.

The foregoing detailed description is given for clearness of understanding only and no unnecessary limitations should be understood therefrom, as modifications will be obvious to those skilled in the art.

I claim:

1. A method of demonstrating the presence of a free fatty acid in a liquid sample, said method comprising the steps of:
   (a) mixing said sample with a reagent comprising a solution of a complex of a long chain cationic surfactant and an anionic dye whereby said free fatty acids react with said complex to liberate said dye from said complex; and,
   (b) observing the resulting color change in said sample.

2. The method of claim 1 wherein said surfactant is a quaternary ammonium cationic surfactant.

3. The method of claim 2 wherein said surfactant is selected from the group consisting of surfactants having the following structures:

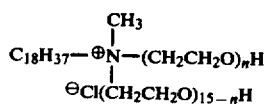

wherein n is an integer between about 6 and 8, inclusive;

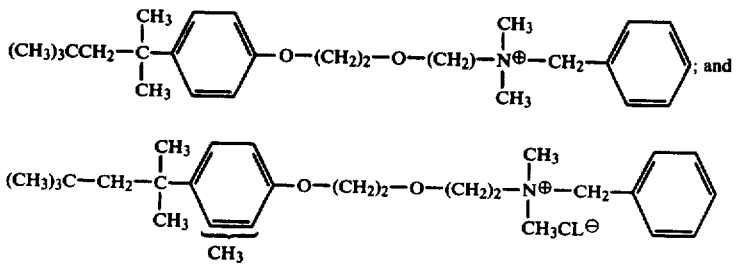

4. The method of claim 2 wherein said dye is selected from the group consisting of azo dyes, sulfonphthalein dyes, triphenylmethane dyes, fluorescein dyes, naphthalenesulfonic acid dyes, anthraquinone dyes, phenoxazine dyes, tricarbocyanine dyes, indigo dyes and acridine dyes.

5. The method of claim 4 wherein said surfactant comprises

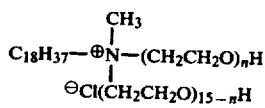

wherein n is an integer between about 6 and 8, inclusive, said dye is a sulfobromphthalein dye, and said surfactant and dye are present in said complex in substantially equimolar amounts.

6. The method of claim 5 wherein said reaction is carried out at a pH of between about 8.5-8.8 in the presence of a buffer.

7. A method of determining the concentration of a free fatty acid in a liquid sample, said method comprising the steps of:
   (a) mixing said sample with a reagent comprising a solution of a complex of a long chain cationic surfactant and an anionic dye whereby said free fatty acid reacts with said complex to liberate said dye from said complex;
   (b) observing the resulting color change in said sample; and,
   (c) comparing the degree of said color change to calibration means.

8. The method of claim 7 wherein said surfactant is a quaternary ammonium cationic surfactant.

9. The method of claim 8 wherein said surfactant is selected from the group consisting of surfactants having the following structures:

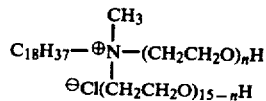

wherein n is an integer between about 6 and 8, inclusive;

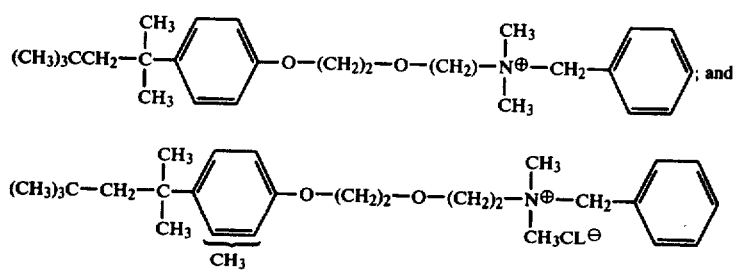

10. The method of claim 8 wherein said dye is selected from the group consisting of azo dyes, sulfonphthalein dyes, triphenylmethane dyes, fluorescein dyes, naphthalenesulfonic acid dyes, anthraquinone dyes, phenoxazine dyes, tricarbocyanine dyes, indigo dyes and acridine dyes.

11. The method of claim 10 wherein said surfactant comprises

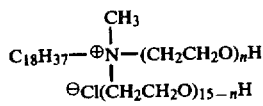

wherein in is an integer between about 6 and 8, inclusive, said dye is a solfobromphthalein dye, and said surfactant and dye are present in said complex in substantially equimolar amounts.

12. The method of claim 11 wherein said reaction is carried out at a pH of between about 8.5-8.8 in the presence of a buffer.

13. A method of demonstrating the presence in a liquid sample of a component which is hydrolyzable to liberate free fatty acids, said method comprising the steps of:
 (a) hydrolyzing said component to liberate said free fatty acids to produce a first reaction mixture;
 (b) mixing said first reaction mixture with a reagent comprising a solution of a complex of a long chain cationic surfactant and an anionic dye whereby said free fatty acids react with said complex to liberate said dye from said complex; and,
 (c) observing the resulting color change in said sample.

14. The method of claim 13 wherein said surfactant is a quaternary ammonium cationic surfactant.

15. The method of claim 14 wherein said surfactant is selected from the group consisting of surfactants having the following structures:

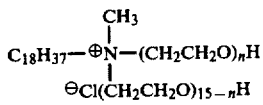

wherein n is an integer between about 6 and 8, inclusive;

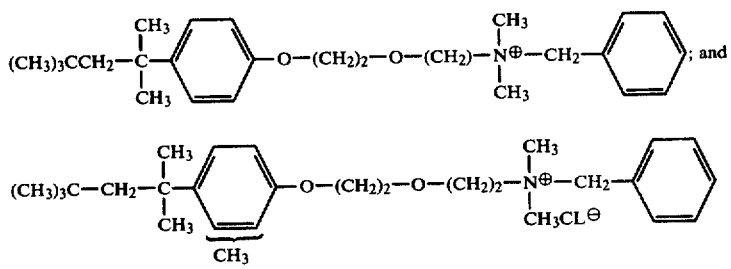

16. The method of claim 14 wherein said dye is selected from the group consisting of azo dyes, sulfonphthalein dyes, triphenylmethane dyes, fluorescein dyes, naphthalenesulfonic acid dyes, anthraquinone dyes, phenoxazine dyes, tricarbocyanine dyes, indigo dyes and acridine dyes.

17. The method of claim 16 wherein said surfactant comprises

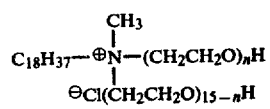

wherein n is an integer between about 6 and 8, inclusive, said dye is a sulfobromphthalein dye, and said surfactant and dye are present in said complex in substantially equimolar amounts.

18. The method of claim 17 wherein said reaction is carried out at a pH of between about 8.5-8.8 in the presence of a buffer.

19. A method of demonstrating the presence in a liquid sample of a component which is hydrolyzable to liberate free fatty acids, said method comprising the steps of:
 (a) hydrolyzing said component with a hydrolase enzyme to liberate said free fatty acids to produce a first reaction mixture;
 (b) mixing said first reaction mixture with a reagent comprising a solution of a complex of a long chain cationic surfactant and an anionic dye whereby said free fatty acids react with said complex to liberate said dye from said complex; and,
 (c) observing the resulting color change in said sample.

20. A method of determining the concentration in a liquid sample of a component which is hydrolyzable to liberate free fatty acids, said method comprising the steps of:
 (a) hydrolyzing said component to liberate said free fatty acids to produce a first reaction mixture; and,
 (b) mixing said first reaction mixture with a reagent comprising a solution of a complex of a long chain cationic surfactant and an anionic dye whereby said free fatty acids react with said complex to liberate said dye from said complex;
 (c) observing the resulting color change in said sample; and,
 (d) comparing the degree of said color change to calibration means.

21. The method of claim 20 wherein said surfactant is a quaternary ammonium cationic surfactant.

22. The method of claim 21 wherein said surfactant is selected from the group consisting of surfactants having the following structures:

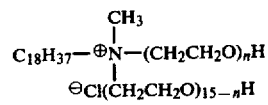

wherein n is an integer between about 6 and 8, inclusive;

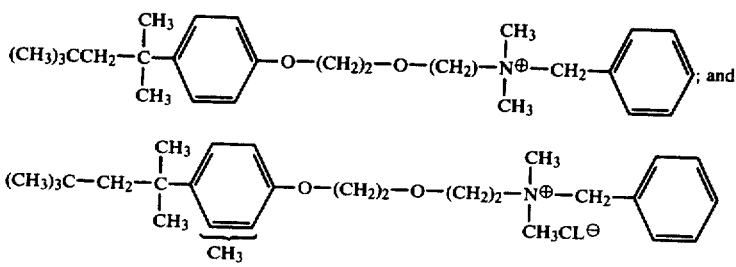

23. The method of claim 1 wherein said dye is selected from the group consisting of azo dyes, sulfonphthalein dyes, triphenylmethane dyes, fluorescein dyes, naphthalenesulfonic acid dyes, anthraquinone dyes, phenoxazine dyes, tricarbocyanine dyes, indigo dyes and acridine dyes.

24. The method of claim 23 wherein said surfactant comprises

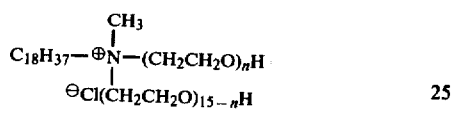

wherein n is an integer between about 6 and 8, inclusive, said dye is a sulfobromphthalein dye, and said surfactant and dye are present in said complex in substantially equimolar amounts.

25. The method of claim 24 wherein said reaction is carried out at a pH of between about 8.5–8.8 in the presence of a buffer.

26. A method of determining the concentration in a liquid sample of a component which is hydrolyzable to liberate free fatty acids, said method comprising the steps of:

(a) hydrolyzing said component with a hydrolase enzyme to liberate said free fatty acids to produce a first reaction mixture;

(b) mixing said first reaction mixture with a reagent comprising a solution of a complex of a long chain cationic surfactant and an anionic dye whereby said free fatty acids react with said complex to liberate said dye from said complex;

(c) observing the resulting color change in said sample; and, (d) comparing the degree of said color change to calibration means.

27. A method of demonstrating the presence of a hydrolase enzyme in a liquid sample, said method comprising the steps of:

(a) mixing said sample with a known amount of a material which is hydrolyzable by said enzyme to liberate fatty acids, and a reagent comprising a complex of a long chain cationic surfactant and an anionic dye whereby said material is hydrolyzed to liberate fatty acids, and said fatty acids react with said complex to liberate said dye; and, (b) observing the resulting color change in said sample.

28. The method of claim 27 wherein said surfactant is a quaternary ammonium cationic surfactant.

29. The method of claim 28 wherein said surfactant is selected from the group consisting of surfactants having the following structures:

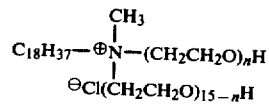

wherein n is an integer between about 6 and 8, inclusive;

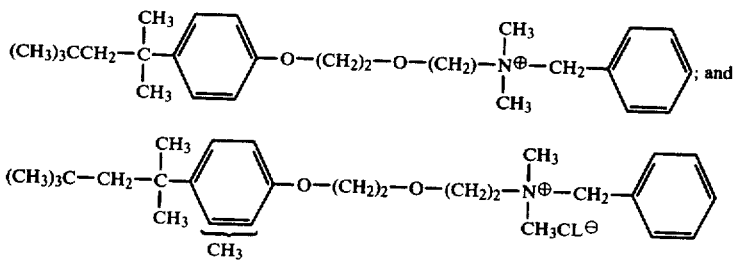

30. The method of claim 28 wherein said dye is selected from the group consisting of azo dyes, sulfonphthalein dyes, triphenylmethane dyes, fluorescein dyes, naphthalenesulfonic acid dyes, anthraquinone dyes, phenoxazine dyes, tricarbocyanine dyes, indigo dyes and acridine dyes.

31. The method of claim 30 wherein said surfactant comprises

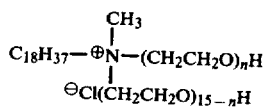

wherein n is an integer between about 6 and 8, inclusive, said dye is a sulfobromphthalein dye, and said surfactant and dye are present in said complex in substantially equimolar amounts.

32. The method of claim 31 wherein said reaction is carried out at a pH of between about 8.5–8.8 in the presence of a buffer.

33. A method of determining the concentration of hydrolase enzyme in a liquid sample, said method comprising the steps of:
(a) mixing said sample with a known amount of a material which is hydrolyzable by said enzyme to liberate fatty acids, and a reagent comprising a complex of a long chain cationic surfactant and an anionic dye whereby said material is hydrolyzed to liberate fatty acids, and said fatty acids react with said complex to liberate said dye;
(b) observing the resulting color change in said sample; and,
(c) comparing said color change with calibration means.

34. The method of claim 33 wherein said surfactant is a quaternary ammonium cationic surfactant.

35. The method of claim 34 wherein said surfactant is selected from the group consisting of surfactants having the following structures:

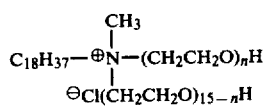

wherein n is an integer between about 6 to 8, inclusive;

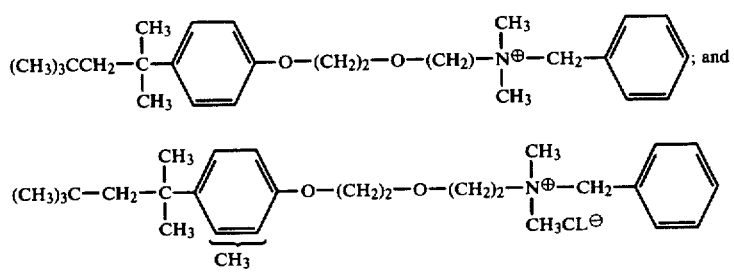

36. The method of claim 34 wherein said dye is selected from the group consisting of azo dyes, sulfonphthalein dyes, triphenylmethane dyes, fluorescein dyes, naphthalenesulfonic acid dyes, anthraquinone dyes, phenoxazine dyes, tricarbocyanine dyes, indigo dyes and acridine dyes.

37. The method of claim 36 wherein said surfactant comprises

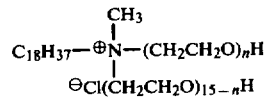

wherein n is an integer between about 6 and 8, inclusive, said dye is a sulfobromphthalein dye, and said surfactant and dye are present in said complex in substantially equimolar amounts.

38. The method of claim 37 wherein said reaction is carried out at a pH of between about 8.5–8.8 in the presence of a buffer.

39. A reagent kit for determining the concentration of a component hydrolyzable by a hydrolase enzyme to liberate fatty acids, said reagent kit comprising first and second containers, said first container containing a solution of said hydrolase enzyme, and said second container containing a solution of a complex of a long chain cationic surfactant and an anionic dye.

40. The reagent kit of claim 39 wherein said surfactant comprises

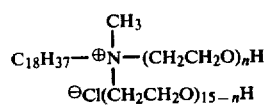

wherein n is an integer between about 6 and 8, inclusive, said dye is a sulfobromphthalein dye, and said surfactant and dye are present in said complex in substantially equimolar amounts.

41. A reagent kit for determining the concentration of a hydrolase enzyme in a sample, said reagent kit comprising first and second containers, said first container containing a material hydrolyzable by said hydrolase enzyme to liberate fatty acids from said material, and said second container containing a solution of a complex of a long chain cationic surfactant and an anionic dye.

42. The reagent kit of claim 41 wherein said surfactant comprises

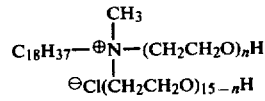

wherein n is an integer between about 6 and 8, inclusive, said dye is a sulfobromphthalein dye, and said surfactant and dye are present in said complex in substantially equimolar amounts.

* * * * *